(12) United States Patent
Choi et al.

(10) Patent No.: US 7,258,694 B1
(45) Date of Patent: Aug. 21, 2007

(54) MEDICAL PUNCH AND SURGICAL PROCEDURE

(75) Inventors: Steven Choi, Mountain View, CA (US); Scott Reed, Monroe, CT (US); Alan Bachman, Milford, CT (US)

(73) Assignee: Origin Medsystems, Inc., San Jose, CA (US)

( * ) Notice: Subject to any disclaimer, the term of this patent is extended or adjusted under 35 U.S.C. 154(b) by 8 days.

(21) Appl. No.: 10/863,097

(22) Filed: Jun. 7, 2004

Related U.S. Application Data

(63) Continuation-in-part of application No. 10/173,997, filed on Jun. 17, 2002.

(51) Int. Cl.
*A61B 17/32* (2006.01)
*A61B 17/3209* (2006.01)

(52) U.S. Cl. .............. 606/184; 606/185; 606/180; 606/179; 606/174

(58) Field of Classification Search ............ 606/184, 606/186
See application file for complete search history.

(56) References Cited

U.S. PATENT DOCUMENTS

| | | | |
|---|---|---|---|
| 2,818,852 A | 1/1958 | Kugler et al. | |
| 3,776,237 A | 12/1973 | Hill et al. | |
| 3,835,860 A | 9/1974 | Garretson | |
| 3,837,345 A | 9/1974 | Matar | |
| 3,867,942 A | 2/1975 | Bellantoni et al. | |
| 4,018,228 A | 4/1977 | Goosen | |
| 4,216,776 A | 8/1980 | Downie et al. | |
| 4,306,570 A | 12/1981 | Matthews | |
| 4,476,864 A | 10/1984 | Tezel | |
| 4,733,663 A | 3/1988 | Farley | |
| 5,129,913 A | 7/1992 | Ruppert | |
| 5,192,294 A | 3/1993 | Blake, III | |
| 5,403,338 A | 4/1995 | Milo | |
| 5,501,698 A | 3/1996 | Roth et al. | |
| D372,310 S | 7/1996 | Hartnett | |
| D372,312 S | 7/1996 | Lange | |
| 5,591,186 A * | 1/1997 | Wurster et al. | ............ 606/185 |
| 5,618,270 A | 4/1997 | Orejola | |
| 5,695,504 A | 12/1997 | Gifford, III et al. | |
| 5,702,412 A | 12/1997 | Popov et al. | |
| 5,752,526 A | 5/1998 | Cosgrove | |
| 5,769,086 A | 6/1998 | Ritchart et al. | |
| 5,817,113 A | 10/1998 | Gifford, III et al. | |
| 5,827,316 A * | 10/1998 | Young et al. | ............ 606/185 |

(Continued)

FOREIGN PATENT DOCUMENTS

WO WO 00/59380 10/2000

(Continued)

*Primary Examiner*—Glenn K. Dawson
(74) *Attorney, Agent, or Firm*—Law Office of Alan W. Cannon

(57) ABSTRACT

A medical punch includes a longitudinally dividable anvil with a reduced cross-sectional dimension facilitating insertion of the anvil into the vessel wall to achieve a clean aperture in the vessel wall by cooperative shearing action of a cutting edge and an anvil edge. In another embodiment, the instrument incorporates a measuring device for determining the thickness of a vessel wall between an anvil and a distal end of a cylindrical structure which together form a caliper, and the measuring device can also constitute a medical punch by cooperative shearing action of a cutting edge and an anvil to achieve a clean aperture in the vessel wall.

23 Claims, 8 Drawing Sheets

U.S. PATENT DOCUMENTS

| | | | |
|---|---|---|---|
| 5,893,369 A | 4/1999 | LeMole | |
| 5,893,865 A | 4/1999 | Swindle et al. | |
| 5,904,697 A | 5/1999 | Gifford, III et al. | |
| 5,910,153 A | 6/1999 | Mayenberger | |
| 5,944,730 A | 8/1999 | Nobles et al. | |
| 5,984,940 A | 11/1999 | Davis et al. | |
| 6,022,367 A * | 2/2000 | Sherts | 606/184 |
| 6,036,710 A | 3/2000 | McGarry et al. | |
| 6,080,173 A | 6/2000 | Williamson, IV et al. | |
| 6,080,175 A | 6/2000 | Hogendijk | |
| 6,080,176 A | 6/2000 | Young | |
| 6,083,238 A | 7/2000 | Alexander, Jr. et al. | |
| 6,142,955 A | 11/2000 | Farascioni et al. | |
| 6,172,321 B1 | 1/2001 | Kanai et al. | |
| 6,176,867 B1 | 1/2001 | Wright | |
| 6,187,022 B1 | 2/2001 | Alexander, Jr. et al. | |
| 6,193,734 B1 | 2/2001 | Bolduc et al. | |
| 6,280,460 B1 | 8/2001 | Bolduc et al. | |
| 6,319,244 B2 | 11/2001 | Suresh et al. | |
| 6,371,965 B2 | 4/2002 | Gifford, III et al. | |
| 6,387,105 B1 | 5/2002 | Gifford, III et al. | |
| 6,416,527 B1 | 7/2002 | Berg et al. | |
| 6,436,054 B1 | 8/2002 | Viola et al. | |
| 6,443,965 B1 | 9/2002 | Gifford, III et al. | |
| 6,447,443 B1 | 9/2002 | Keogh et al. | |
| 6,451,034 B1 | 9/2002 | Gifford, III et al. | |
| 6,461,320 B1 | 10/2002 | Yencho et al. | |
| 6,478,028 B1 | 11/2002 | Paolitto et al. | |
| 6,478,029 B1 | 11/2002 | Boyd et al. | |
| 6,491,704 B2 | 12/2002 | Gifford, III et al. | |
| 6,491,705 B2 | 12/2002 | Gifford, III et al. | |
| 6,494,211 B1 | 12/2002 | Boyd et al. | |
| 6,517,558 B2 | 2/2003 | Gittings et al. | |
| 6,517,561 B1 | 2/2003 | Phillips | |
| 6,537,287 B1 | 3/2003 | Yencho et al. | |
| 6,537,288 B2 | 3/2003 | Vargas et al. | |
| 6,565,582 B2 | 5/2003 | Gifford, III et al. | |
| 6,605,098 B2 | 8/2003 | Nobis et al. | |
| 6,613,069 B2 | 9/2003 | Boyd et al. | |
| 6,651,671 B1 | 11/2003 | Donlon et al. | |
| 6,666,832 B1 | 12/2003 | Carranza et al. | |
| 6,673,085 B1 | 1/2004 | Berg | |
| 6,673,088 B1 | 1/2004 | Vargas et al. | |
| 6,676,678 B2 | 1/2004 | Gifford, III et al. | |
| 6,682,541 B1 | 1/2004 | Gifford, III et al. | |
| 6,699,256 B2 | 3/2004 | Logan et al. | |
| 6,699,257 B2 | 3/2004 | Gifford, III et al. | |
| 6,709,441 B2 | 3/2004 | Bolduc et al. | |
| 6,719,769 B2 | 4/2004 | Donohoe et al. | |
| 6,719,785 B2 | 4/2004 | Schoon et al. | |
| 2002/0082614 A1 | 6/2002 | Logan et al. | |
| 2005/0101983 A1* | 5/2005 | Loshakove et al. | 606/185 |
| 2005/0154411 A1* | 7/2005 | Breznock et al. | 606/184 |

FOREIGN PATENT DOCUMENTS

| | | |
|---|---|---|
| WO | WO 02/32293 A2 | 4/2002 |
| WO | WO 02/32323 A2 | 4/2002 |
| WO | WO 02/32324 A2 | 4/2002 |
| WO | WO 02/058568 A1 | 8/2002 |

* cited by examiner

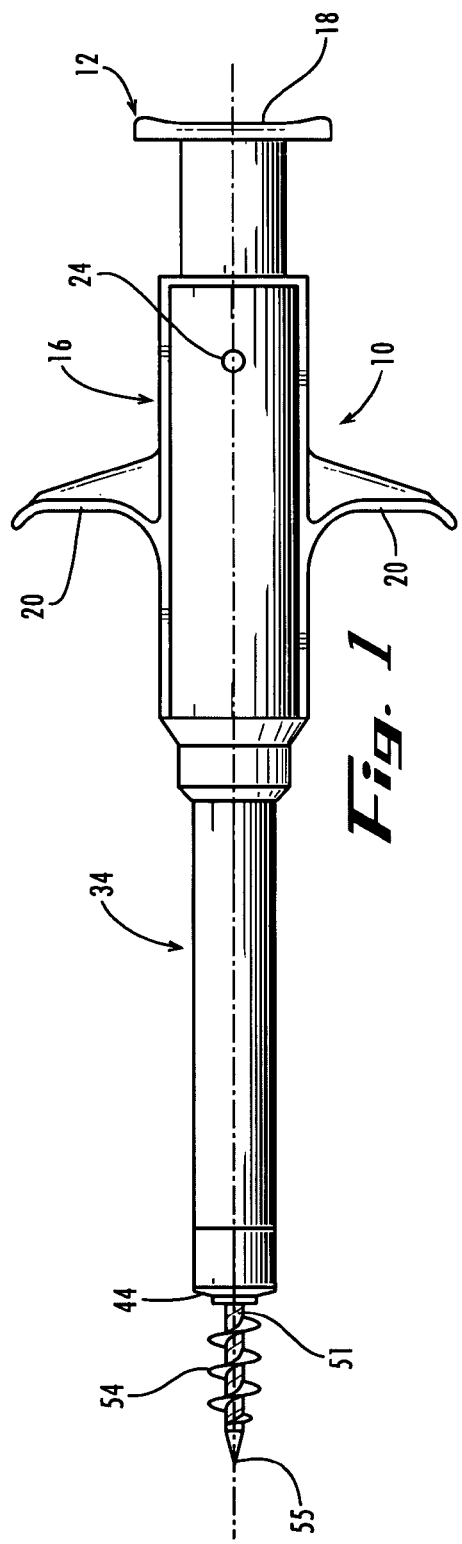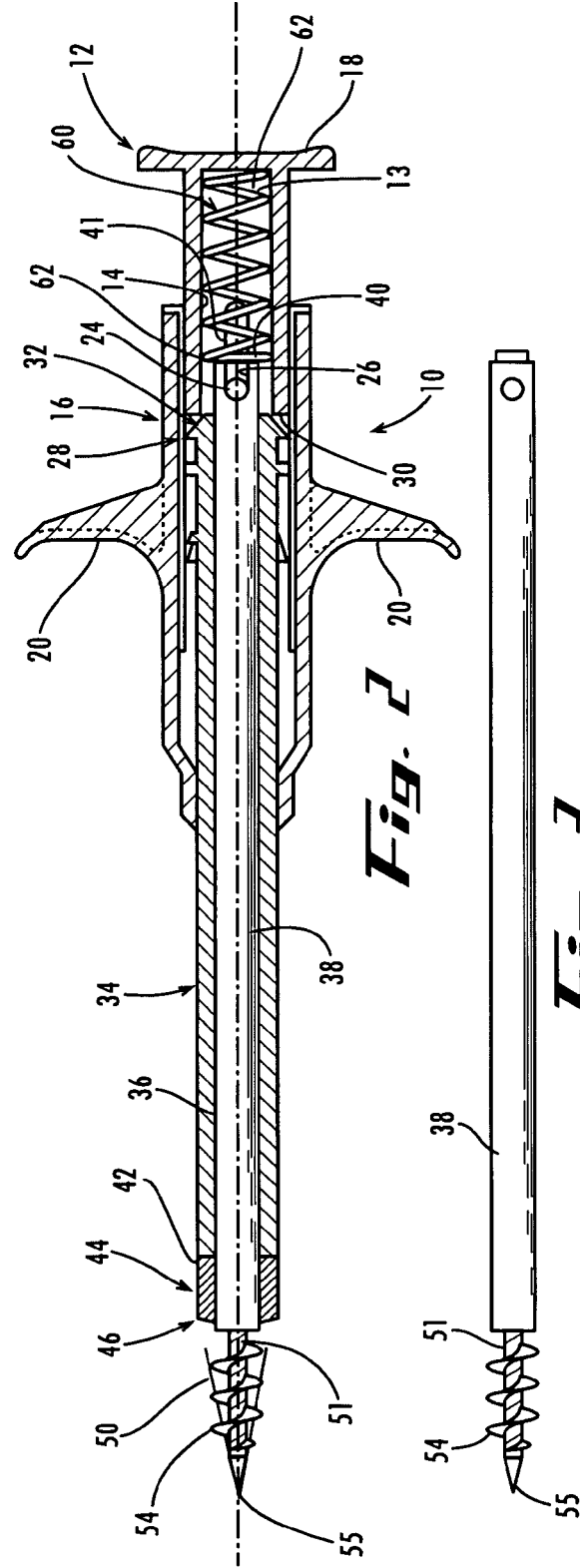

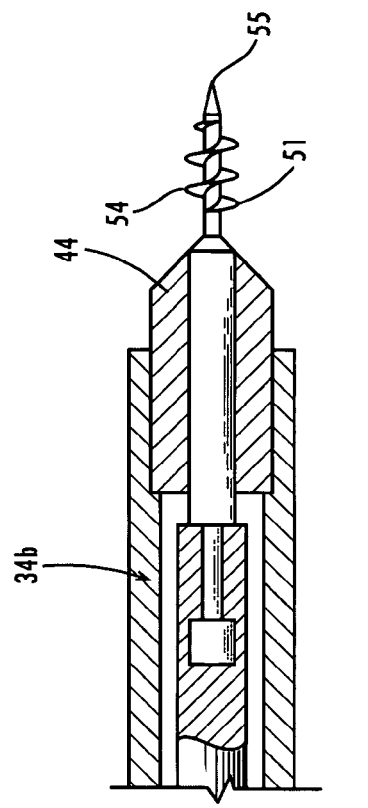
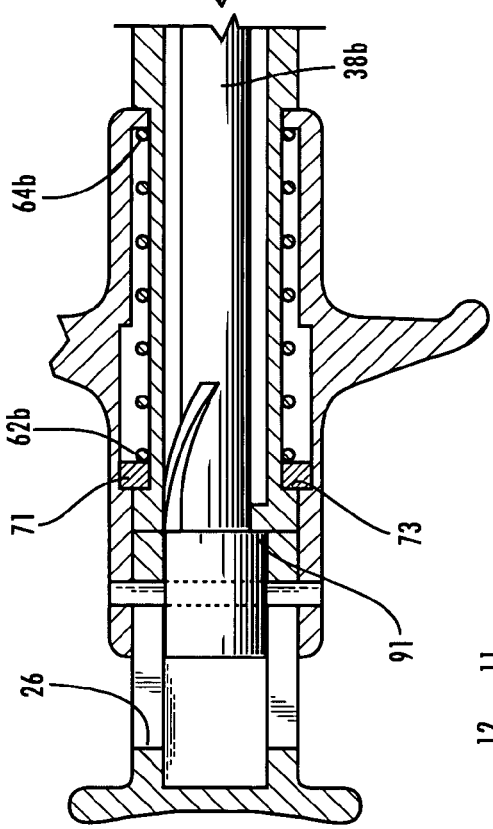
Fig. 4
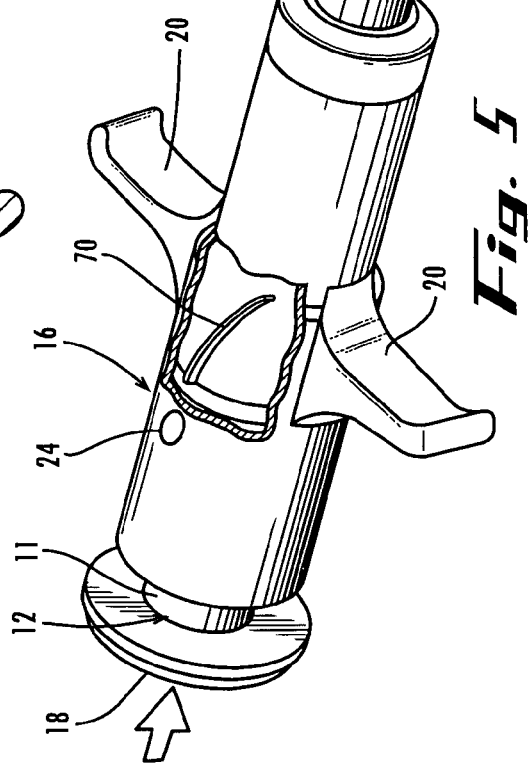
Fig. 5

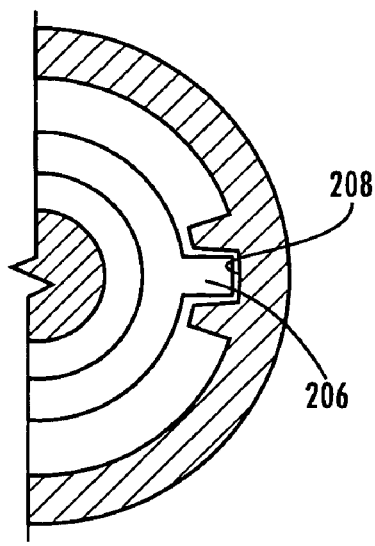
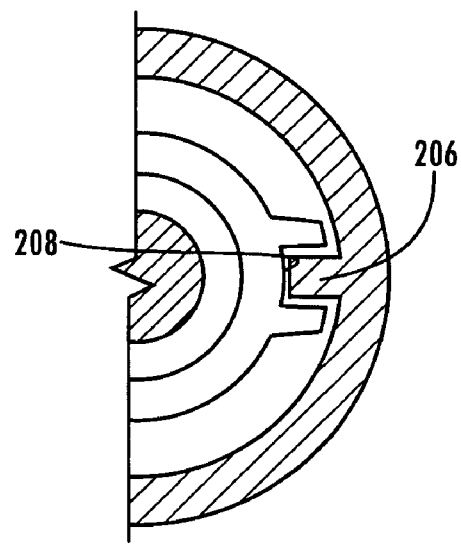
Fig. 6
Fig. 7
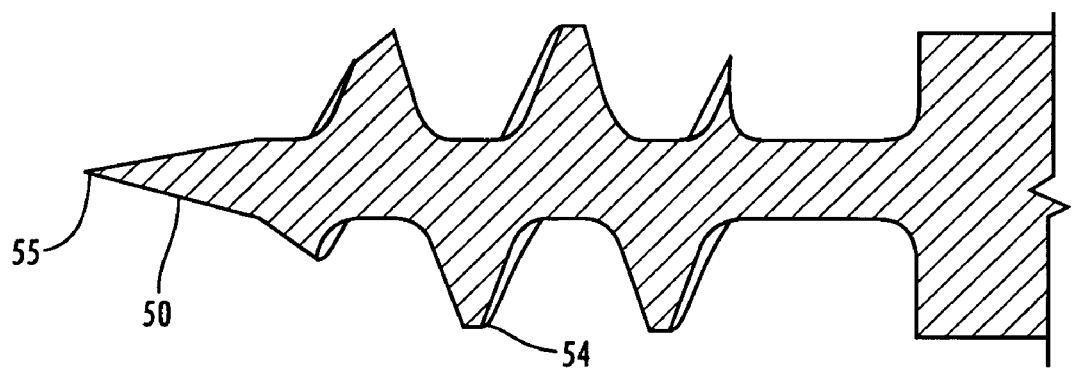
Fig. 8a
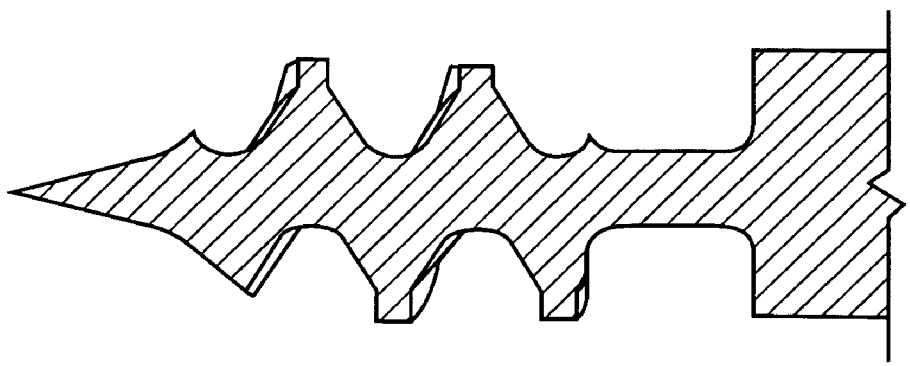
Fig. 8b

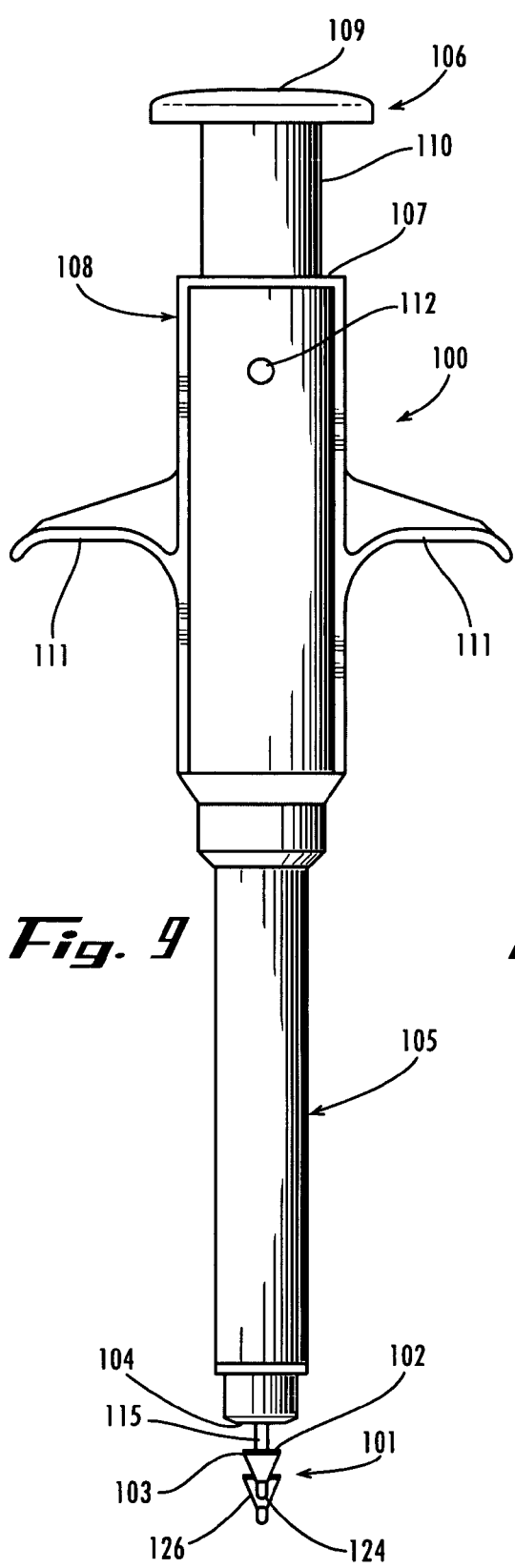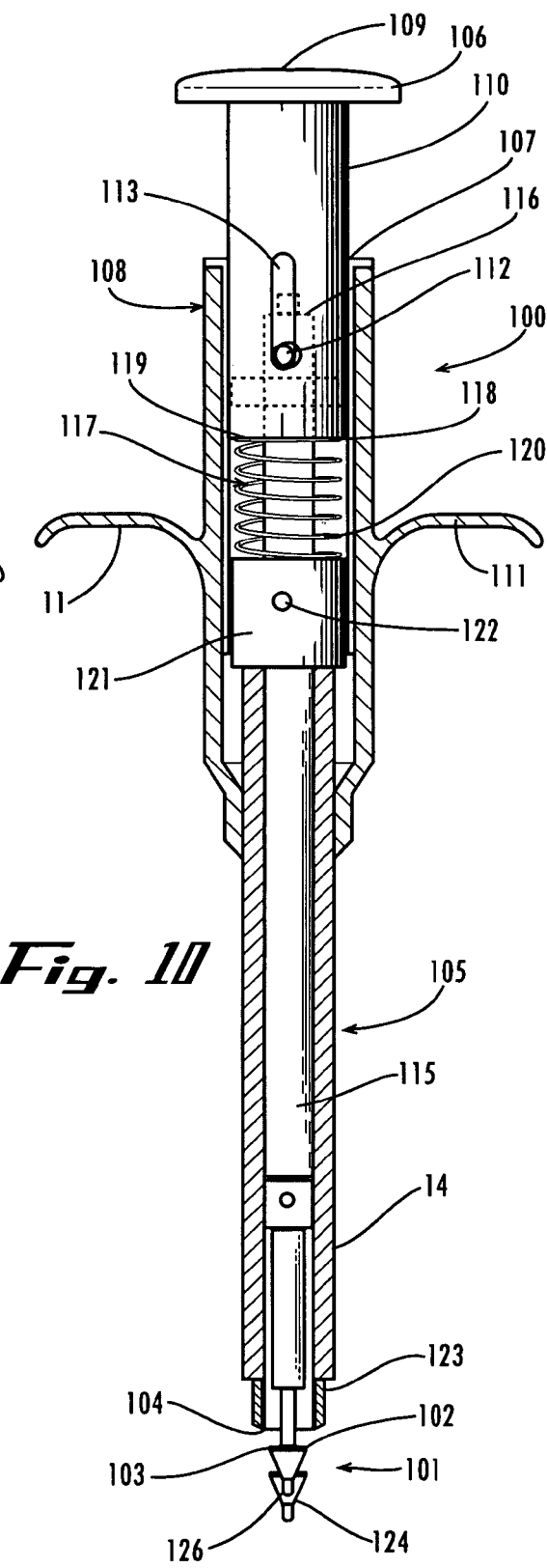

MEDICAL PUNCH AND SURGICAL PROCEDURE

RELATED APPLICATIONS

This application is a continuation-in-part of the U.S. patent application Ser. No. 10/173,997, entitled "Medical Punch and Surgical Procedure" filed on Jun. 17, 2002, which subject matter is incorporated herein by this reference to form a part hereof.

FIELD OF THE INVENTION

This invention relates to medical punches and more particularly to a split anvil punch for cutting a clean aperture in vessel tissue, and a measuring device for determining the thickness of the vessel wall.

BACKGROUND OF THE INVENTION

Medical punches are used in certain surgical procedures to cut tissue. For example, a blood vessel is cut using a medical punch, and surgical scalpels and/or scissors are first used to form an incision in the vessel. Typically, the medical punch includes an anvil which is first inserted into the incision. Then, a tube of the medical punch extends, and a cutting edge of the tube slides along the anvil, thus shearing the vessel tissue. Finally, the anvil and cutting edge of the tube of the medical punch are withdrawn from the incision following completion of such a cut.

The cutting edge of the distal end of the tube in conventional medical punches commonly includes a flat cutting edge having effectively no shearing angle and requiring the entire cutting edge to cut simultaneously into the vessel tissue during the cutting operation. Because the conventional medical punch accomplishes cutting of tissue by shearing, and effects this shearing by sliding a cutting edge past the anvil, the vessel tissue does not remain centralized and may shift slightly during the cut, and the cut thus produced is not always clean and accurate because some fraying may result. Moreover, because the vessel tissue is commonly very durable and the cutting edge of the tube is flat, the entire peripheral surface of the cut is effected at the same time, requiring a lot of hand pressure to successfully manipulate the medical punch through the tissue-cutting procedure. Additionally, because the vessel tissue does not remain centralized and shifts during the cutting operation, the vessel tissue has a tendency to gather to one side or the other of the anvil of the device. This often causes the device to become jammed with vessel tissue.

There is a need for an improved medical punch which does not have a tendency to jam, which can be used to obtain a very clean and accurate cut without any fraying, and which can be operated without excessive hand pressure. Further, with advances in other anastomosis-related technologies, there is a need for an improved medical punch that can be used on a blood vessel that is pressurized by blood flowing through it without having to place a clamp on the vessel to divert the blood away from the punched site.

In conventional medical punches, the anvil must be forced into the initial incision made by scalpels and/or scissors. This can result in problems if the incision is not large enough. Inserting the anvil into this small incision can result in tearing of the vessel tissue, and in difficulty operating the punch if the anvil must be awkwardly forced into position. The anvil can be more easily inserted if the incision is too large, but the procedure may result in leakage around the edges of the opening that is made by the punch and that is smaller than the insertion incision.

Medical punches disclosed in the prior art sometimes include a sharp tip that is pressed against the vessel wall to both make the incision and to then insert the anvil into the incision in one step. This avoids the need for a separate instrument to make the initial incision. However, this again involves difficulty in forcing the wider anvil base through a small hole in the vessel. This can result in tearing of vessel tissue and awkwardness in manipulation while trying to insert the anvil through the vessel wall. Putting a great deal of pressure on the punch to force the sharp tip into the vessel may involve the risk of forcing the tip too far and puncturing the opposite side of the vessel wall. Additionally, such a sharp-tipped device must be inserted into the body cavity and into the vicinity of the appropriate vessel without accidentally puncturing any other tissue in the path. A smaller anvil base could be incorporated into a one-step punch to allow for easier insertion. However, such a smaller anvil may not cut a sufficiently large hole as may not hold the intima layer of the vessel wall sufficiently firmly against the media layer after insertion into the vessel, resulting in a potentially dangerous separation of tissue layers within the vessel.

It is necessary in some surgical procedures to get an accurate measurement of the vessel wall thickness before using a medical punch to make an aperture in the vessel wall. Currently, epi-aortic scans allow for this form of measurement, but involve introduction of additional medical devices with concomitant risks to the patient.

There is a need for an improved medical punch that minimizes the problems of vessel wall tearing and difficult manipulation during anvil insertion, while still having a sufficient anvil width to clamp tissue layers within a vessel wall against separation during formation of an aperture in the vessel wall. There is a need for a one-step punch with little risk of puncturing or traumatizing unintended tissues. There is also a need for a device for measuring the thickness of a vessel wall easily and accurately during the tissue punching procedure, and without the need for introduction of a separate measuring device into the patient.

SUMMARY OF THE INVENTION

In accordance with one embodiment of the present invention a medical punch has a helical leading edge that facilitates screwing the punch into a pressurized vessel without having to make a separate incision or using a clamp, and the helical leading edge serves as a helical cutting edge that facilitates scissor-like shearing action. The punch includes a hollow body member, the end of which provides a mating cutting edge. A shaft located within the hollow body member includes a screw-like anvil that cooperates with the cutting edge at the distal end of the hollow body member. Sliding the hollow body member along the shaft causes the cutting edge at the distal end to move past the helical edge of the anvil to form a shearing action around the perimeter of the cutting edge at the end of the hollow body member. This shearing achieves a clean and accurate cut of vessel tissues using only nominal hand pressure to effect the cut.

In one embodiment, the medical punch includes a thumb button, which is pushable toward a finger grip and is engaged with the hollow body member. The finger grip has a pin secured therein, and the pin is received within a slot on the thumb button. A compression spring is located within the thumb button having a first end engaged with the thumb button and a second end engaged with a shaft that carries the screw-like anvil. A cutting edge on the end of the hollow body member slides over the helical edge of the screw-like anvil that is supported on the shaft, which is secured by the pin to the finger grip. Pushing the thumb button into the finger grip thus causes the hollow body to move generally axially relative to the shaft and causes the distal cutting edge to slide past the helical cutting edge of the anvil.

In another embodiment, the cutting edge at the distal end of the hollow body member and the helical cutting edge along the screw-like anvil relatively rotate in response to axial movement of the shaft and anvil within the hollow body member.

In another embodiment of the present invention, the medical punch has a penetrating structure with a longitudinally dividing anvil that facilitates insertion into the vessel wall. The anvil separates into two or more sections that can be moved distally or proximally relative to one another to form a split-anvil configuration. Before penetration, the various sections are positioned with the wider portions of the anvils in one or more sections near to the narrower portions of the anvils in the other sections. Thus, the cross-sectional dimension of the translated anvil sections at any one position along the length of the penetrating structure in the split-anvil configuration is less than the cross-sectional dimension of the fully assembled base of the anvil. This facilitates insertion of the anvil into the vessel wall since the anvil is narrower along its length, and this minimizes the risk of tearing or awkward manipulation of the punch. After the divided anvil is inserted fully into the vessel, the anvil can be reassembled by moving the sections of the anvil proximally or distally relative to one another to form a full-anvil configuration in which all anvil sections are longitudinally aligned to form the complete anvil.

Also in accordance with this embodiment, the punch includes a hollow body member, the distal end of which includes a cutting edge. A shaft is located within the hollow body member and attached to the dividing anvil that cooperates with the cutting edge at the distal end of the hollow body member to provide tissue-shearing action around.

Also in this embodiment, the medical punch includes a thumb button and finger grips that can be pulled toward the thumb button. The dividable anvil sections are supported by a dividable shaft. As the finger grips are pulled toward the thumb button, the divided anvil is assembled into a complete anvil. The complete anvil cooperates with the cutting edge to shear a hole in tissue.

In another embodiment, the dividable anvil includes a cutting device or a blade that runs longitudinally and distally through the anvil from the distal tip to the anvil base. The cutting device or blade can be attached to one of the sections of the dividable anvil, or can be retractable and movable proximally or distally relative to the anvil sections.

In another embodiment, the cutting edge at the distal end of the hollow body member and the anvil rotate relatively in response to axial movement of the shaft and anvil within the hollow body member.

In another embodiment, the instrument incorporates a measuring device for determining the thickness of a vessel wall. This device includes an anvil that is inserted into a vessel, and also includes a hollow body member with a distal end that can be manipulated into contact with the outer vessel wall. After tissue penetration, the anvil is pulled proximally against the innermost intima layer of the vessel. Sliding the hollow body member along the shaft causes the distal end of the hollow body member to move against the outermost adventitia layer of the vessel. The anvil and the distal end of the hollow body member form a caliper that sandwiches the tissue layers in the vessel wall and allows measurement of the tissue thickness. The thickness measurement can be recorded by graduated markings, or by a digital display disposed on the device.

Also in this embodiment, the measuring device includes a thumb button, which is pushable toward a finger grip. A compression spring is located beneath the thumb button and is engaged with the hollow body member. The finger grip has a pin secured therein, and the pin is received within a slot on the thumb button. A reference edge on the distal end of the hollow body member slides over the edge of the anvil that is supported on the shaft which is secured by the pin to the finger grip. Pushing the thumb button toward the finger grip thus causes the hollow body to move generally axially relative to the shaft to move the reference edge toward the anvil edge.

In another embodiment, the instrument incorporates a measuring device within a medical punch. The distal end of the hollow body member includes a cutting edge that slides over an anvil to shear tissue in a vessel wall that is disposed against the anvil after the tissue thickness is measured.

BRIEF DESCRIPTION OF THE DRAWINGS

FIG. 1 is a side, elevational view of a medical punch in accordance with one embodiment of the present invention.

FIG. 2 is a cross-sectional view of the medical punch shown in FIG. 1.

FIG. 3 is a plan view of the shaft and attached helical anvil in the embodiment of FIG. 1.

FIG. 4 is a sectional view of another embodiment of a medical punch in accordance with the present invention.

FIG. 5 is a perspective view with partial cut-away of the medical punch shown in FIG. 4.

FIG. 6 is a partial sectional view of one spiraling mechanism in the medical punch shown in FIGS. 4 and 5.

FIG. 7 is a partial sectional view of another spiraling mechanism in the medical punch shown in FIGS. 4 and 5.

FIG. 8a is a partial sectional view of the anvil for the punch of FIG. 1.

FIG. 8b is a partial sectional view of another anvil for the punch of FIG. 1.

FIG. 9 is a side, elevational view of a medical punch in accordance with one embodiment of the present invention.

FIG. 10 is a sectional view of the medical punch shown in FIG. 9.

DETAILED DESCRIPTION OF THE INVENTION

Figure 11:
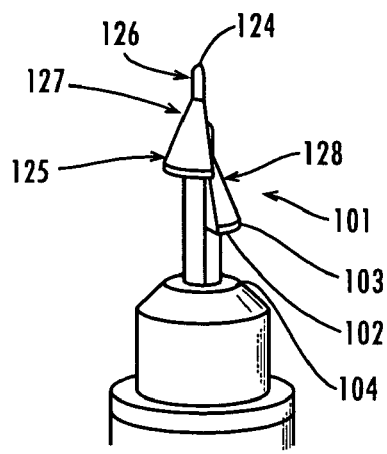
FIG. 11 is a side view of the dividing anvil for the punch of FIG. 9 in the split-anvil configuration.

Referring now to FIGS. 1 and 2, there is shown one embodiment of a medical punch 10 in accordance with the present invention. Instead of having a single cutting edge with effectively no shear angle, the medical punch 10 includes a screw-like anvil with a helical cutting edge 54 that cooperates with the cutting edge 44 at the end of the hollow body member 34 to create a scissor-like shearing action around the perimeter of cutting edge 44. As a result, the medical punch 10 can be used to achieve a clean and accurate cut of vessel tissue. Additionally, the medical punch 10 eliminates the need for excessive hand pressure to effect the shearing of tissue which progresses along the helical edge 54 in response to the cutting edge 44 sliding over the helical edge 54. In addition, the helical edge 54 facilitates augering the anvil 51 into the wall of a vessel such as the aorta carrying blood under pressure without having to make a separate initial incision or having to clamp off the vessel upstream of the penetration.

The medical punch 10 is shaped and designed to be utilized by a surgeon in one hand. The medical punch 10 includes a thumb button 12 pushable into a central opening 14 in a finger grip body 16. The thumb button 12 includes a thumb seat 18 which is shaped to be engaged by a thumb of the surgeon, and the thumb button 12 includes a hollow cylindrical portion 11 which extends into the central bore 14 of the finger grip body 16. The finger grip body 16 includes finger grips 20 that are shaped to be engaged by the first and second fingers of the surgeon's hand. Secured in the central opening 14 of the finger grip body 16 is a pin 24, which is received in slots 26 formed in the hollow cylindrical portion 11 of the thumb button 12. The slots 26 slide across the pin 24 as the thumb button 12 is pushed into the central bore 14 of the finger grip body 16. As the thumb button 12 is pushed into the central bore 14 in the finger grip body 16, the pin 24 restricts rotation and the extent to which the thumb button 12 can be pushed into the central bore 14.

A bottom portion 28 of the thumb button 12 has an opening 30 for snap-on, securable engagement with a top portion 32 of a hollow body member 34. This snap-on engagement assures that the hollow body member 34 moves along with the thumb button 12 as the thumb button 12 is pushed into, or pulled out from, the central bore 14 of the finger grip body 16.

The hollow body member 34 has a central bore 36 through which shaft 38 extends. The pin 24 extends through a top portion 40 of the shaft 38 and is secured thereto to restrict rotation and axial movement of the shaft 38 with respect to the finger grip body 16 as the thumb button 12 is pushed into the central bore 14 in the finger grip body 16.

Spring 60 is positioned in compression within the hollow interior of the thumb button 12, with the top 62 engaged with a flange 13 within the hollow cylindrical portion 11 of the thumb button 12, and with a bottom 64 engaged with a shoulder 41 on the top portion 40 of the shaft 38. The compression spring 60 resiliently urges the thumb button 12 out from the central bore 14 of the finger grip body 16 against the thumb button 12 being pushed therein. Providing the compressing spring 60 within the thumb button 12 permits the finger grip body 16 to be designed and shaped to facilitate positioning the finger grips 20 relatively close together. As a result, the medical punch 10 is easier to use because it more easily fits in the surgeon's hand.

The shaft 38 does not move as the thumb button 12 is pushed into the finger grip body 16 because the top portion 40 of the shaft is secured to the shaft 38 by the pin 24. However, the engagement of the bottom portion 28 of the thumb button 12 with the top portion 32 of the hollow body member 34 assures that the hollow body member 34 slides along the shaft 38 as the thumb button 12 is pushed. Therefore, the hollow body member 34 slides along the shaft 38, which remains stationary as the thumb button 12 is pushed into the finger grip body 16. At the end 42 of the hollow body member 34 is a cutting edge 44 which preferably comprises a cylinder having an end portion 46 that may be disposed at an acute or right angle relative to the axis of shaft 38.

In accordance with present invention, the anvil 51 is formed as a screw-like member as shown in FIGS. 1-3 and 8a having a continuous outer edge 54 that is helically disposed along the axial extent of the anvil from a distal point 55 to an axial position that may be within the hollow body member 34. The distal point has a taper 50 of 15 degrees for easier penetration of tissue. And, the gradual helical transition from a minor diameter near the distal point 55 to the outside diameter of the helical edge 54 prevents tearing of vessel-wall tissue during penetration of the vessel wall by the anvil 51. The outer helical edge 54 of the anvil 51 cooperates with the cutting edge 44 at the distal end of the hollow body member 34 to provide scissor-like shearing action that progresses around the perimeter of the cutting edge 44 and along the helical outer edge 54 of the anvil 51 as the hollow body member 34 slides over the anvil 51 in a direction toward the distal point 55. In this way, the progression of the contiguous cutting edges provides a shearing action that significantly reduces the required hand pressure on the thumb button 12 relative to the finger grips 20 in order to cut out a round aperture in vessel tissue. In addition, the angled or slopped "lands" of the anvil toward the helical cutting edge, as shown in FIG. 8a, promote smoother cutting of tissue against the overlaying cutting edge 44 than is attainable with the squared or normal-edged anvil shown in FIG. 8b.

In operation, the distal point 55 is positioned at a selected site on a vessel (e.g., the aorta) and is pressed sufficiently via the finger grip body 16, 20 to penetrate the vessel tissue. Then, the finger grip body 16 is rotated in screw-like manner to promote deeper penetration of the screw-like shape of the anvil 51 into the vessel tissue. This allows slow, controlled penetration into a vessel under pressure internally without making a separate initial incision or using a clamp on the vessel. The continued screw-like motion anchors the anvil 51 firmly within the vessel tissue at the selected surgical site (e.g. for anastomosis with a graft vessel at the surgical site). After the anvil 51 is rotated at least one or more rotations into the vessel tissue, the screw-like anvil serves as a plug in the resilient vessel tissue to inhibit leaking from the vessel of liquid (e.g., blood) under pressure, and also serves to position the cutting edge 44 of the hollow body member 34 in close proximity to the vessel tissue. Then, in response to hand pressure applied to the thumb button 12 toward the finger grips 20, the cutting edge 44 at the distal end of the hollow body member 34 slides axially over the helical edge 54 of the anvil 51 to produce a scissor-like action that rotates around the perimeter of the cutting edge 44. In this way, vessel tissue anchored on the screw-like anvil 51 is progressively sheared to form a clean, round aperture with only slight exertion of hand pressure. Additionally, with an exterior of the hollow body member 34 that tapers axially from the distal cutting edge 44, the hollow body member 34 may be inserted into the clean, round aperture thus formed in vessel tissue to serve as a plug in cooperation with the resilient properties of vessel tissue to inhibit any substantial loss of liquid under pressure from the vessel. Additionally, the plug of tissue thus severed remains anchored on the screw-like anvil 51 for convenient retrieval from within the vessel upon withdrawal from the vessel of the entire assembly of anvil 51 and extended hollow body member 34.

Preferably, the thumb button 12, finger grip body 16, and hollow body member 34 of the medical punch 10 are all formed of plastic, and the pin 24, anvil 51, shaft 38, compression spring 60, and the cutting edge 44 of the medical punch 10 are all formed of metal. However, such compositions are, of course, not required in accordance with the present invention but may only be preferred for low-cost manufacture of a disposable one-use medical punch.

Pushing the thumb button 12 toward the finger grips 20 drives the thumb button 12 into the central bore 14 in the finger grip body 16 while the slots 26 on the thumb button 12 ride along the pin 24 in the finger grip 16. Additionally, the hollow body member 34 slides along the shaft 38 with the hollow body member 34 in snap-on engagement with the opening 30 in the bottom portion 28 of the thumb button 12. As the thumb button 12 is pushed into the finger grip 16, the spring 60 compresses within the thumb button 12 against the shaft 38, and the shaft 38 remains stationary relative to the finger grip body 16 because of the pin 24 positioned between the finger grip body 16 and the shaft 38. As the hollow body member 34 slides along the shaft 38, the cutting edge 44 at the end of the hollow body member 34 moves toward the anvil 51 at the end of the shaft 38.

After cutting vessel tissue in this manner, the medical punch 10 can be withdrawn from the severed-tissue aperture, with the anvil 51, the cutting edge 44 and the severed tissue collectively withdrawn. Then, the thumb button 12 can be released. The compression spring 60 urges the thumb button 12 axially away from the finger grip body 16.

In the event that a severed portion of the vessel tissue gets caught between the anvil 51 and the cutting edge 44, thus temporarily jamming the medical punch 10, the thumb button 12 can be pulled from the central bore 14 of the finger grip body 16 to release the severed portion of tissue and to slide the hollow body member 16 in relation to the shaft 38. The cutting edge 44 slides away from the anvil 51 as the thumb button 12 is pulled. Consequently, pulling the thumb button 12 axially away from the finger grip body 16 should cause the severed portion to dislodge from between the anvil 51 and the cutting edge 44.

A cut of tissue is effected gradually as the thumb button 12 is pressed toward the finger grips 20. Thus, by cutting tissue at only a portion of the peripheral cutting edge 44 at one time, less hand pressure is required on the medical punch 10 to effect the cutting operation. Additionally, by cutting only a portion of the peripheral edge of the cut at one time, the medical punch 10 produces a cleaner cut of a more precise hole in the vessel tissue. Furthermore, by screwing the anvil 51 into the vessel tissue, the medical punch 10 is kept generally stabilized during the cutting operation, and the tissue does not tend to shift relative to the punch 10. And, no initial incision into a vessel is required to insert the anvil 51 with the concomitant benefit of avoiding formation of an initial incision larger than the hole required by the anvil as with a conventional medical punch.

In another embodiment of the present invention, as illustrated in FIGS. 4 and 5, there is shown a similar screw-like anvil 51 disposed at the distal end of the inner shaft 38*b* which is positioned within the outer hollow body member 34*b*. In this embodiment, the hollow body member 34*b* carries a cutting edge 44 at the distal end thereof to cooperate in contiguous relationship with the helical edge 54 of the anvil 51 to provide scissor-like action around the perimeter of cutting edge 44 in response to relative axial movement of the anvil 51 and cutting edge 44.

In addition, the hollow body member 34*b* also rotates relative to the anvil 51 during such relative axial movements thereof. This rotation of the hollow body member 34*b* and distal cutting-edge 44 relative to the anvil 51 and helical cutting edge 54 is accomplished in one embodiment, as illustrated in FIG. 7, using a pin or other protrusion 206 disposed on the outer hollow body member 16 that rides in a spiral groove 208 disposed on the shaft attached to the distal cutting edge 44, as shown in FIG. 7. The spiral groove may traverse approximately 10-25° of angular rotation about an elongated central axis of the assembly over the relative axial travel distance of the cutting edge 44 and anvil 51. Of course, the orientations of pin 206 and mating groove 208 may be reversed on the finger grip body 16 and hollow shaft as shown in FIG. 6, and the spiral groove may progress in either rotational direction with axial movement relative to the mating pin or protrusion 206. However, a favored rotation is in the opposite rotation direction of the helical edge 54 of the anvil 51 to accelerate completion of one full rotation of the scissor-like shearing action about the perimeter of the cutting edge 44 in response to relative axial movement of the anvil 51 and the cutting edge 44 in a direction toward the distal point 55 of the anvil 51. The finger grip body 16 remains pinned 24 to the inner shaft 38*b* supporting the anvil 51, and such pinned attachment also restricts rotational movement of the thumb button 12 that includes the longitudinal grooves 26 which pass along the pin 24. Thus, rotational movement between the inner shaft 38*b* and the thumb button 12 occurs at the thrust bearing interface 91 of those components. A coil spring 62*b* disposed in compression between the distal end of the finger grip body 16 and the proximal end of the hollow body member 34 resiliently urges the cutting edge 44 edge away from the distal point 55 of the anvil 51.

In operation, the distal point 55 of the anvil 51 is pressed into vessel tissue at a selected surgical site to penetrate the vessel. The finger grip body 16 is rotated to screw the helical anvil 51 into the vessel tissue, at least one or more full turns of the helix into the tissue, to thereby firmly anchor the medical punch 10 in tissue at the surgical site. The thumb button 12 is then pressed toward the finger grips 20 to slide the cutting edge 44 carried by hollow body member 34 over the helical edge 54 of the anvil 51 in a direction toward the distal point 51. This motion also rotates the hollow body member 34 within the finger grip body 16 in response to the spiral groove 70, 208 on the one member transversing the pin or protrusion 206 attached to the other member. In this way, the distal cutting edge 44 rotates against the vessel tissue as the cutting edge 44 slides over the helical cutting edge 54 of the anvil 51 a sufficient distance to complete scissor-like shearing action around one full convolute of the helix relative to the distal cutting edge 44.

Therefore, the medical punch of the present invention promotes progressive shearing action along a helical cutting edge in cooperation with a cylindrical distal cutting edge that moves axially, or axially and rotationally, relative to the helical cutting edge in response to light hand pressure exerted between an actuating thumb button and finger grips.

Referring now to FIGS. 9 and 10, there is shown an embodiment of a medical punch 100 in accordance with the present invention. The medical punch 100 includes a penetrating structure in the form of an anvil 101 at its distal end. At the proximal side of the anvil 101 is an anvil base 102 which is surrounded by an anvil edge 103 that cooperates with the cutting edge 104 at the distal end of the hollow body member 105 to achieve a clean and accurate cut of vessel tissue. The anvil 101 divides longitudinally into sections that are movable proximally and distally relative to one another. Thus, the anvil 101 can be divided to form a split anvil before insertion into the vessel wall to reduce the cross-sectional dimension of the anvil sections for easier insertion into the tissue. The anvil 101 can be reassembled after insertion into the vessel to form a complete anvil that can be pulled proximally against the intima layer of the vessel to confine the vessel wall in place during the punching step. In this manner, the complete anvil assists in keeping the intima layer from separating from the other tissue layers in the vessel wall during formation of the aperture in the vessel wall.

The medical punch 100 includes a thumb button 106 that can be pushed into a central opening 107 in a finger grip body 108. The thumb button 106 includes a thumb seat 109 that is shaped to be engaged by a thumb of the surgeon, and the thumb button 106 includes a hollow cylindrical portion 110 that extends into the central opening 107 of the finger grip body 108. The finger grip body 108 includes finger grips 111 that are shaped to be engaged by the first and second fingers of the surgeon's hand. As the thumb button 106 is pressed, the finger grips 111 are pulled in the direction of the thumb button 106. A pin 112 extends through slot 113 formed in the hollow cylindrical portion 110 of the thumb button 106. One side of the pin 112 is secured to the finger grip body 108 while the other side is secured to a shaft 115 that translates the dividable anvil 101. The pin 112 slides along the slot 113 as the finger grips 111 are pulled in the direction of the thumb button 106. The pin 112 restricts rotation and the extent to which the thumb button 106 can be pushed into the central opening 107 of the finger grip body 108. The hollow body member 105 has a central bore 114 through which shaft 115 extends.

In one embodiment, the anvil exists in a split-anvil configuration when the device is at rest and the thumb button 106 is not being pressed. In this embodiment, the pin 112 is secured to the finger grip body 108 and it extends through a slot 113 formed in the hollow cylindrical portion 110 of the thumb button 106 and then connects at the other side to shaft 115. In this embodiment, the pin 112 specifically connects to the section of the shaft 115 that connects to and translates the distal-most segment of the anvil when the anvil is in a split-anvil configuration. The pin 112 restricts rotation and axial movement of the shaft 115 with respect to the finger grip body 108 as the finger grips 111 are pulled toward the thumb button 106.

Spring 117 is positioned in compression below the base 118 of the hollow cylindrical portion 110 of the thumb button 106. The top 119 of the spring 117 is engaged with the base 118 of the hollow cylindrical portion 110, and the bottom 120 of the spring 117 is engaged with a cylindrical support member 121. Center pin 122 is secured at one end to the cylindrical support member 121, and the pin 122 extends through a slot (not shown) in the section of shaft 115 that connects to and translates the distal-most segment of the anvil 101. The other end of the center pin 122 is attached to the section of the shaft 115 that connects to and translates the proximal-most segment of the anvil when the anvil 101 is in a split-anvil configuration. Center pin 122 assists in holding the two segments of the shaft 115 and the anvil segments together, allowing the device 100 to function in the manner described herein.

The compression spring 117 resiliently urges the thumb button 106 proximally out from the central opening 107 of the finger grip body 108 and the spring 117 resiliently urges the cylindrical support member 121 toward the distal end of the device 100. As the thumb button 106 is pressed and the finger grips 111 are pulled toward the thumb button 106, the distal-most section of the anvil 101 moves axially toward the cutting edge 104. This movement is provided by the pin 112 that connects to the segment of the shaft 115 that translates the distal-most segment of the anvil 101. Pin 112 rides along slot 113 as the finger grips 111 are pulled toward the thumb button 106, thereby pulling the distal-most segment of the anvil 101 proximally.

Independent travel of the distal-most section of the anvil 101 is limited by the center pin 122, which rides along a slot (not shown) in the segment of shaft 115 that connects to the distal-most segment of the anvil 101. When the center pin 122 has traveled the length of the slot (not shown), the distal-most section of the anvil 101 will be substantially lined up with the proximal-most portion of the anvil 101, to form a complete-anvil configuration. At this point, the distal-most anvil section bears upon and engages the proximal-most anvil section, causing them to move together in complete-anvil configuration against the cutting edge 104 and into the hollow body member 105. Specifically, a negative structure on the distal-most segment of the anvil 101 engages a positive structure in the proximal-most segment of the anvil 101, thereby causing the formation of a complete anvil 101 that can be moved proximally toward the cutting edge 104. For example, the positive structure may be a horizontal bar on the shaft 115 of the proximal-most anvil segment, and this horizontal bar may slide within an opening in the shaft of the distal-most segment as the distal-most segment is translated. When the horizontal bar has slid the full length of the opening and can slide no further, the shaft of the proximal anvil segment is engaged and the proximal anvil segment begins to move with the distal anvil segment in complete-anvil configuration.

Once the divided anvil 101 is assembled into a complete anvil 101, the finger grips 111 can be further pulled toward the thumb button 106 to move the complete anvil 101 further proximally, toward the cutting edge 104, and into the hollow body member 105. Releasing the finger grips 111 allows the anvil 101 to move distally, out of the hollow body member 105, and to resume its original resting position in a split-anvil configuration.

In the embodiment described above, the anvil 101 is in a split-anvil configuration when the anvil is inserted into a vessel. The finger grips 111 are pulled toward the thumb button 106 once the divided anvil 101 is inside the vessel, and the anvil 101 is then assembled into a complete-anvil configuration while inside the vessel. The complete anvil 101 is then pulled proximally against the intima layer of the vessel, thereby pressing the adventitia layer of the vessel against the cutting edge 104 of hollow body member 105. The anvil 101 is then pulled into the hollow body member 105 to sever a hole in the tissue. The piece of severed tissue is trapped against the anvil 101 within the hollow body member 105, and is thus safely retained within the device and prevented from release within the vessel. The device 100 can then be withdrawn from the patient's body. Releasing the finger grips 111 allows the anvil 101 to move distally out of the hollow body member 105, thereby releasing the severed piece of tissue that can then be removed from the device.

In other embodiments, the proximal-most anvil segment translates distally to engage the distal-most anvil segment, forming a complete-anvil configuration. The complete anvil 101 is then translated proximally against the cutting edge 104 and into the hollow body member 105. In this embodiment, the spring 117 is positioned on the opposite side of the cylindrical support member 121, thus the spring 117 is located distally from the cylindrical support member 121. Pressing the thumb button 106 and pulling the finger grips 111 thus pushes the proximal-most segment of the anvil toward the distal-most segment to form a complete anvil, and the spring bias is used to draw the complete anvil proximally, into the hollow body member 105.

In still other embodiments, the anvil is in complete-anvil configuration, inside the hollow body member 105, when the punch is at rest and the thumb button 106 is not being pressed. In this embodiment, the thumb button 106 is pressed to cause the anvil to exit the hollow body member 105 and to translate a section of the anvil 101 either distally or proximally to form a split-anvil configuration. Partial release of the thumb button 106 causes the translated section of the anvil 101 to resume its original position in a complete-anvil configuration. Further release of the thumb button 106 causes the complete anvil 101 to be retracted into the hollow body member 105. In this embodiment, the thumb button 106 is pressed to form a split anvil that is inserted into a vessel. The thumb button 106 is partially released to reassemble the anvil while inside the vessel. The further release of the thumb button translates the complete anvil proximally against the cutting edge 104 and into the hollow body member 105 to sever a hole in the tissue.

In further embodiments, the cutting edge 104 can be translated distally relative to the anvil 101 sections. Thus, when the anvil is inserted into the vessel, the cutting edge 104 can be translated distally against the vessel wall to sever a hole in the tissue. The cutting edge 104 slides over the assembled anvil 101 trapping the severed tissue within the hollow body member 105.

In other embodiments, the device is configured to have an anvil 101 that can be divided into a plurality of sections that can be of the same or different sizes and shapes. In these embodiments, the various anvil sections each are formed with complementary shapes that allow each anvil segment to be engaged by another anvil segment as the segments are moved into a complete-anvil configuration. Additionally, these embodiments include a number of pins akin to pin 122 of device 100. These various pins perform the function of holding all of the anvil segments together, similar to the function of pin 122 in holding the two anvil segments together in device 100.

In accordance with present invention, the dividable anvil 101, as shown in FIGS. 11-14, includes at least two sections that can be moved proximally or distally relative to one another, as described above. FIGS. 11-14 illustrate the dividable anvil 101 as having two sections, but the anvil 101 may be divided into a plurality of sections that may all be of the same or different sizes and shapes. The anvil 101 includes a distal tip 124 that is rounded, but may have many other forms, including a sharp point, or a beveled edge. The rounded distal tip has an advantage over sharp-tipped devices of minimizing the risk of puncturing the opposite side of the vessel wall during insertion of the anvil into the vessel. Additionally, the surgeon is less likely to accidentally injure other body tissues when introducing the instrument into the body cavity of the patient, or when bringing the instrument into the vicinity of the vessel to be punched. A conical section 125 converges distally from the anvil base 102. FIGS. 11-14 show the conical section 125 terminating in a cylindrical section 126 of the anvil 101. However, the anvil 101 and the anvil components may have various other forms, including having the conical section 125 extend all the way to the distal tip 124, having the conical section converge distally from the anvil base 102 at different angles, or having a differently-shaped section replace the cylindrical section 126. The anvil 101 connects to shaft 115 at the anvil base 102.

The anvil 101 divides into at least two sections, 127, 128 as illustrated in FIGS. 11-14. The sections are movable proximally and distally relative to each other. One or more sections can be moved to a configuration in which the narrowest part of the section is brought into proximity with the widest part of the other sections, thereby forming a split-anvil configuration. This configuration of the sections ensures that the cross-sectional dimension of the split anvil at any one point along its length is less than the cross-sectional dimension of the assembled anvil. The reduced cross-section facilitates easier insertion of the anvil 101 into the vessel because the maximum width of the anvil base 102 does not have to be forced through the vessel wall. This minimizes the chances of tearing the tissue during insertion and facing awkward manipulation of the punch when trying to force a large anvil into a vessel.

FIG. 11 illustrates an example of one type of split-anvil configuration of the device. FIG. 11 shows the first section 127 translated distally relative to the second section 128 so that the cylindrical section 126 (narrowest portion) of the second section 127 is near to the anvil base 102 (widest portion) of the first section 128. FIG. 11 illustrates that the shaft 115 of the anvil 101 is also divided into two or more sections, and at least one or more of the sections are movable proximally and distally relative to one another. Each shaft section moves in conjunction with its corresponding anvil section, allowing the anvil sections to be translated independently of one another or at least one section to be translated independently of the other.

Figure 12:
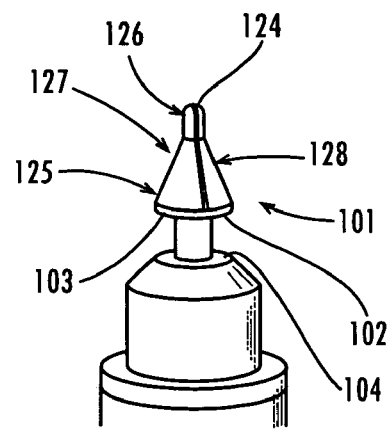
FIG. 12 is a side view of the dividing anvil for the punch of FIG. 9 in the full-anvil configuration.
Figure 13:
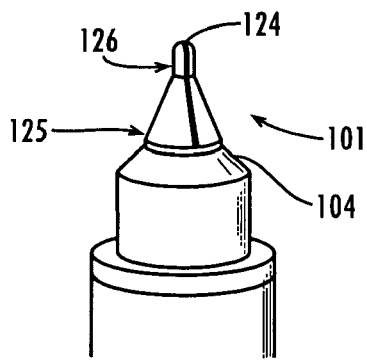
FIG. 13 is a side view of the hollow body member advancing over the anvil of the punch of FIG. 9.
Figure 14:
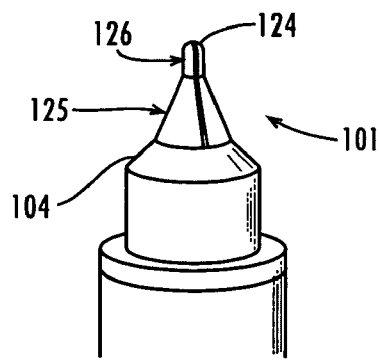
FIG. 14 is a side view of the hollow body member fully advanced distally over the anvil of the punch of FIG. 9.

FIG. 12 illustrates the complete-anvil configuration. At least one or more of the sections of the anvil 101 may be translated distally or proximally relative to one another to reassemble the anvil. In FIG. 12, the first section 127 is positioned proximal to a point where the anvil base 102 of the first section 127 is in proximity to the anvil base 102 of the second section 128. Thus, the split anvil is reassembled into a complete anvil after insertion into the vessel, and the complete width of the anvil holds the internal, intima layer of the vessel against the other vessel layers during punching, thereby avoiding a potentially dangerous separation of tissue layers. FIG. 13 shows the cutting edge 104 of the hollow body member 105 near the anvil edge 103, and FIG. 14 shows the anvil 101 entering the hollow body member 105. The cutting edge 104 cooperates with the anvil edge 103 to shear a hole in the vessel wall. The assembled anvil 101 holds the tissue plug in place against the anvil base 102 during this shearing and the plug of tissue is retained within the tube when the instrument is withdrawn from the patient.

Figure 18:
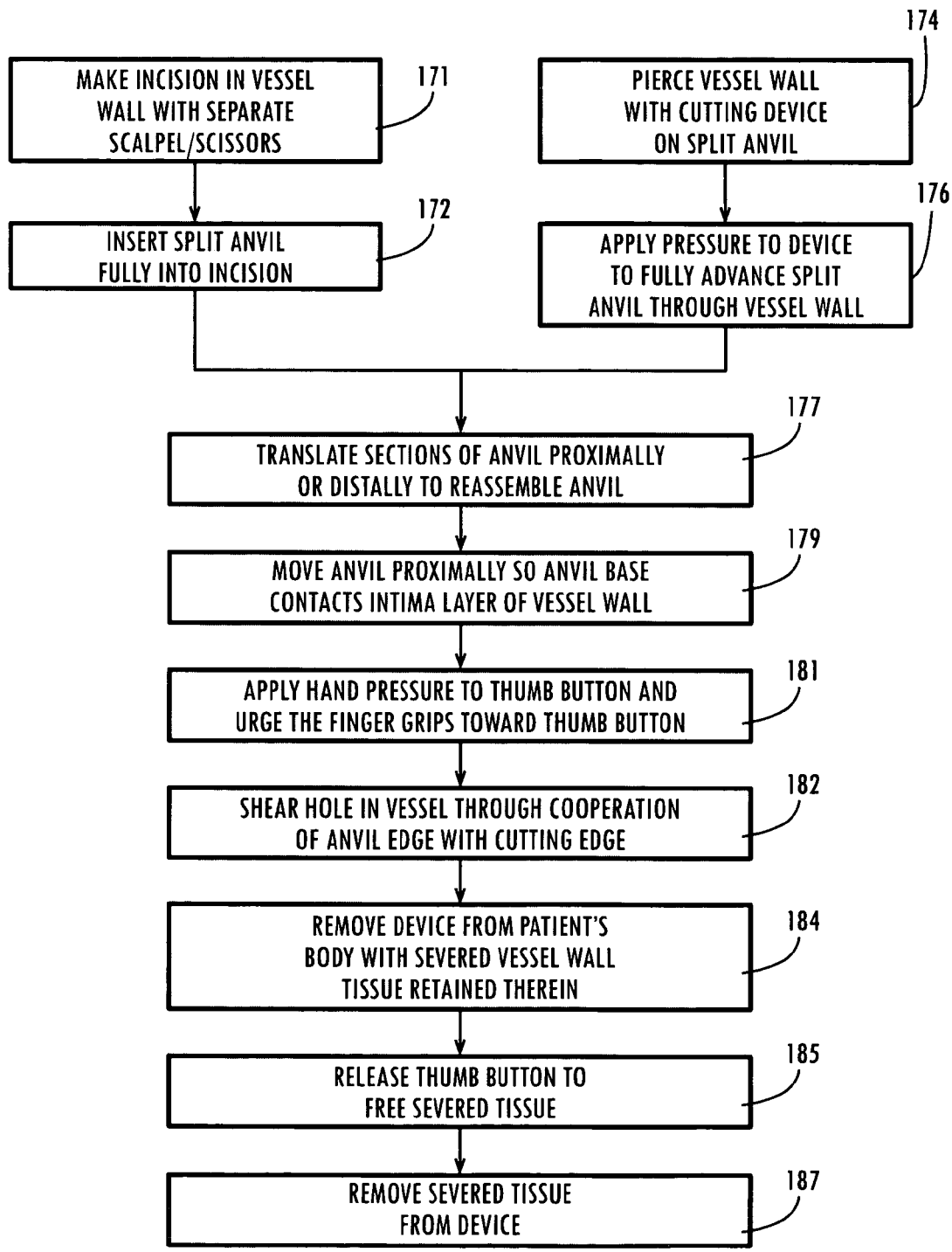
FIG. 18 is a flow chart illustrating the surgical procedure according to one method embodiment of the present invention.

Referring now to FIG. 18, there is shown a flow chart that illustrates a method embodiment of the present invention, as described below with reference to FIGS. 10-14. The flow chart demonstrates the method of use of a two-step punch in which an initial incision is made in the vessel before inserting the anvil. The chart also demonstrates the method of use of a one-step punch in which no initial incision is made. In the two-step punch, an initial incision is formed 171 in the vessel wall at a selected site on the vessel by a separate scalpel and/or scissors. The anvil is inserted 172 into the initial incision in a controlled manner since the operator does not face the difficulty of inserting the complete cross-sectional dimension of the anvil into the vessel. The rounded distal tip 124 allows the surgeon to avoid injury to the opposite side of the vessel wall. Once all of the sections of the anvil 101 have been fully inserted through the vessel wall, one or more of the sections are relatively translated 177 to reassemble the anvil 101 into the complete-anvil configuration. The anvil may then be moved proximally 179 so that the anvil base 102 contacts the inside layer of the vessel in preparation for the punching step. Then, in response to hand pressure applied 181 to the thumb button 106 and pulling of the finger grips 111 toward the thumb button 106, the cutting edge 104 cooperates with the anvil edge 103 to shear 182 a hole in the vessel. With the complete anvil bracing the internal vessel layer against the outer layers, the cutting edge forms a clean aperture in the vessel tissue. Additionally, the plug of tissue thus severed remains anchored on the anvil base 102 for convenient retrieval from within the vessel upon removal 184 from the patient's body of the entire assembly of anvil and extended hollow body member. The thumb button 106 is then released 185 and the severed tissue can be removed 187 from the device.

In the event that a severed portion of the vessel tissue gets caught between the anvil 101 and the cutting edge 104, thus temporarily jamming the medical punch 100, the thumb button 106 can be pulled from the central opening 107 of the finger grip body 108 and the finger grips 111 pulled away from the thumb button 106 to release the severed portion of tissue. The tissue is dislodged from between the anvil 101 and the cutting edge 104 by sliding the anvil 101 out of the hollow body member 105.

Preferably, the thumb button 106, finger grip body 108, and hollow body member 105 of the medical punch 100 are all formed of bioinert plastic, and the pin 1112, anvil 101, shaft 115, compression spring 117, and cutting edge 104 of the medical punch 100 are all formed of biologically compatible metal. However, such compositions are not required in accordance with the present invention, but may only be preferred for low-cost manufacture of a disposable one-use medical punch.

Figure 15:
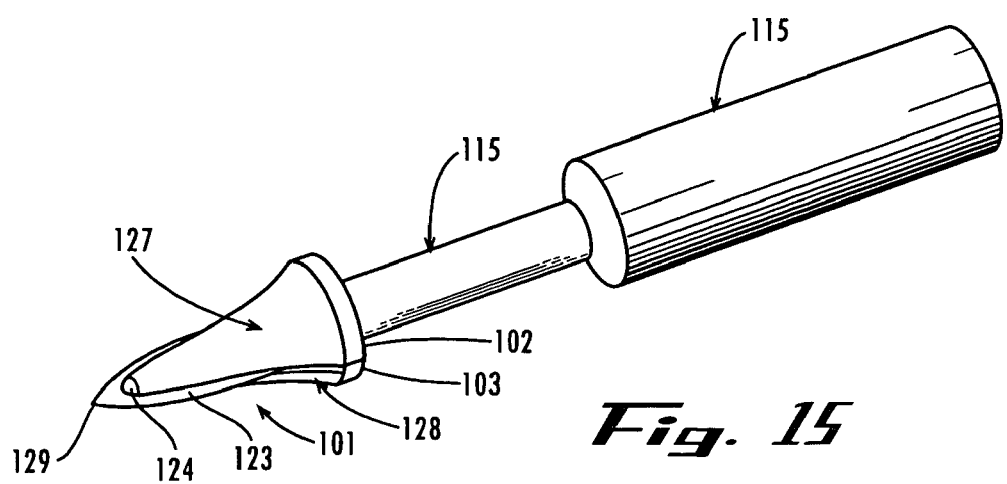
FIG. 15 is a side view of another embodiment of the dividing anvil with integrated cutting device.
Figure 16:
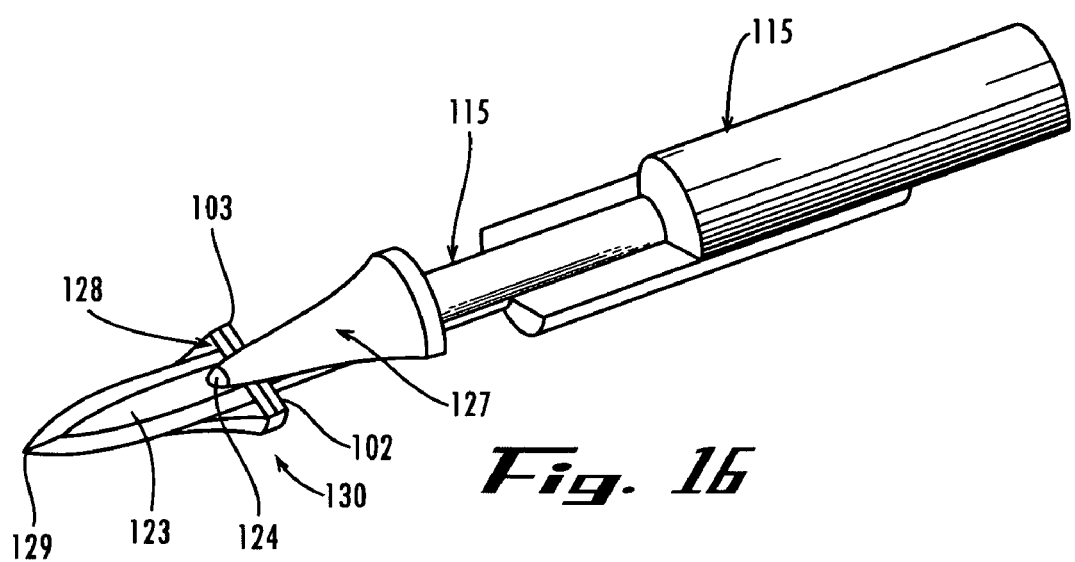
FIG. 16 is a side view of the dividing anvil of FIG. 15 in the split-anvil configuration.

In another embodiment of the anvil of the present invention, as illustrated in FIGS. 15 and 16, there is shown a similar dividable anvil 130 disposed at the distal end of the inner shaft 115. Though only the distal half of the device is illustrated, the device may be configured similar to device 100 or may have some other configuration. The anvil 130 in this embodiment includes a distal tip 124 and a surrounding anvil edge 103 disposed proximal to the distal tip 124. The anvil 130 is shown having a conical shape that converges from an anvil base 102 toward the distal tip 124. However, the anvil 130 and the anvil components may have various shapes and converge at various angles from the anvil base 102. In FIGS. 15 and 16, the anvil 130 is shown as having a first section 127 and a second section 128 that are movable proximally and distally relative to each other. Also, the shaft 1115 is shown as having two sections that both correspond with a section of the anvil and that are movable proximally and distally relative to each other. FIGS. 15 and 16 also show a cutting device 123 that is located between the first section 127 and the second section 128 of the dividing anvil 130. The cutting device 123 is a sharp blade or any other form of sharp structure for piercing tissue. The cutting device 123 is shown as being attached to the second section 128, and the first section 127 may slide over the cutting device 123 to form a split-anvil configuration as shown in FIG. 16.

As shown in FIG. 15, the tip 129 of the cutting device 123 extends distally past the distal tip 124 of the anvil 130. However, the first section 127 may also be longer than the second section 128 so the rounded distal tip 124 of the first section 127 extends past the sharp tip 129 of the cutting device 123 when the finger grips 111 are pulled toward the thumb button 106 to reassemble the anvil. Thus, the sharp tip 129 of the instrument is masked by the longer rounded tip 124 of the first section 127. This ability to mask the sharp tip allows the surgeon to safely introduce the punch 100 into the patient's body and position the punch in proximity to the target vessel for severing a hole in the vessel. Once the punch 100 is position in proximity to the vessel to be incised, the thumb button 109 can be released to expose sharp tip 129. The vessel can then be incised by the sharp tip 129 of the punch.

The cutting device 123 may also be retractable, and thus movable proximally and distally relative to the first section 127 and the second section 128. In this embodiment, the shaft 115 is hollow to allow a member (not shown) attached to the cutting device 123 to be moved inside the device. The member (not shown) may be manipulated to retract or extend the blade during a surgical procedure. Retracting the blade into the instrument assists in protecting against collateral injury to tissue as the instrument is introduced into the body cavity. Additionally, after the cutting device 123 initially penetrates into the vessel, the cutting device 123 may be retracted before the anvil 130 is inserted any farther, thus protecting the opposite side of the vessel wall from injury. Of course, the anvil 130 and the shaft 115 may be divided into numerous sections that are independently movable, and the cutting device 123 may be divided into numerous independently movable sections as well.

In operation, this embodiment of an anvil includes a cutting device 123 that facilitates a one-step punch procedure so the step of making an initial incision in the vessel with a separate scalpel or scissors is not necessary. There is shown a method embodiment of the present invention in the flow chart of FIG. 18 that is described below with reference to FIGS. 15 and 16. The tip 129 of cutting device 123 is pressed against the vessel wall to pierce the tissue 174, and pressure is applied to the device to fully advance 176 the anvil 130 into the vessel in one step with minimal effort due to the reduced cross-section of the split anvil. After the anvil 130 has fully penetrated the vessel wall, the sections of the anvil 130 are translated 177 proximally or distally relative to one another to form a complete-anvil configuration as shown in FIG. 15. The surgeon may then apply hand pressure 181 to the device and shear 182 an aperture in the vessel wall in a manner as previously described herein. The punch with the severed tissue inside is removed 184 from the patient's body, the thumb button is released 185, and the severed tissue is removed from the punch 187.

In another embodiment, the hollow body member 105 rotates relative to the anvil 130 during such relative axial movements thereof. In operation, the distal tip 124 of the anvil 101 is inserted into the vessel tissue at a selected surgical site to penetrate the vessel. Once the anvil has been inserted into the tissue, the finger grips 111 are then pulled toward the thumb button 106 to rotate the hollow body member 105 within the finger grip body 108 relative to the spiral groove (not shown) in the finger grip body 108. This moves the pin, which is attached to the shaft 115, along the spiral groove in finger grip body 108. In this way, the distal cutting edge 104 rotates against the vessel tissue as the tissue is positioned between the cutting edge 104 and the anvil edge 103, thereby shearing a section of vessel tissue. For example, the device 100 can include a mechanism similar to those shown in FIGS. 6 and 7, in which a pin or other protrusion 206 disposed on the finger grip body 108 rides in a spiral groove 208 disposed on the shaft that is attached to the distal cutting edge 104, as shown in FIG. 7. The spiral groove may traverse approximately 10-25° of angular rotation about an elongated central axis of the assembly over the relative axial travel distance of the cutting edge 104 and anvil 101. Of course, the orientations of pin 206 and mating groove 208 may be reversed on the finger grip body 108 and shaft as shown in FIG. 6, and the spiral groove may progress in either rotational direction with axial movement relative to the mating pin or protrusion 206.

Figure 17:
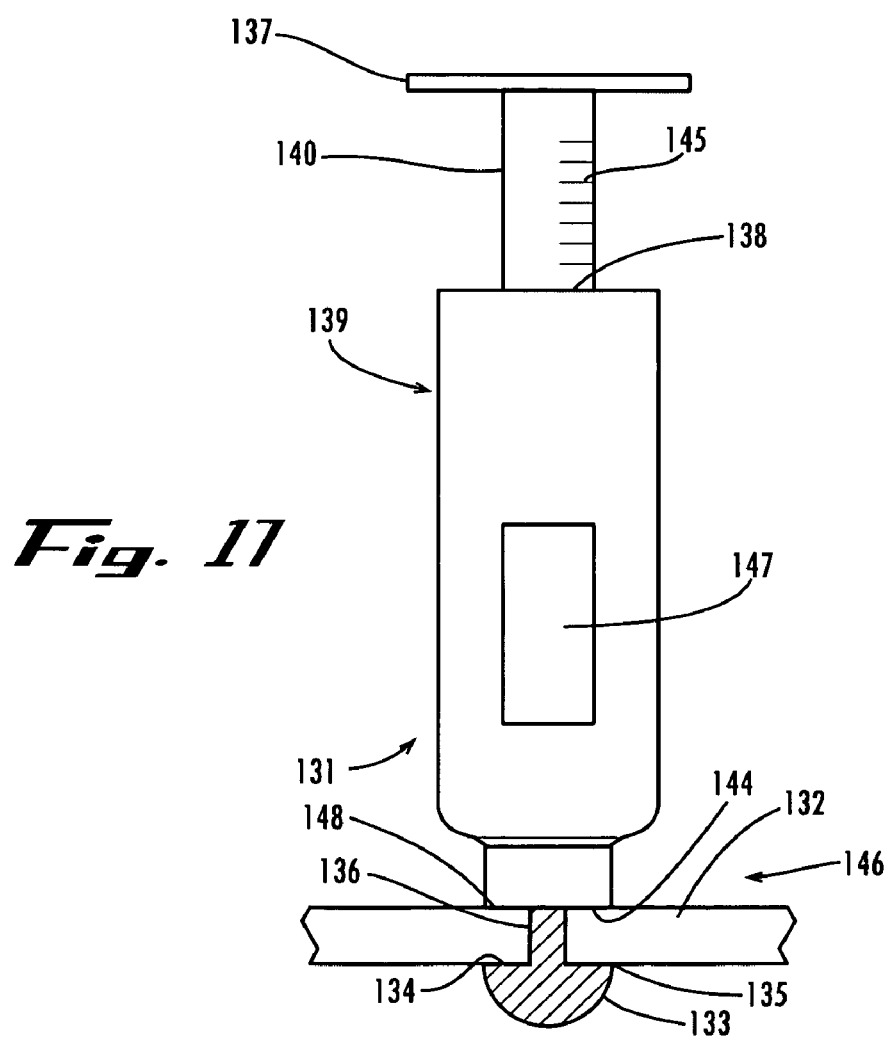
FIG. 17 is a side view of the embodiment of a measuring device in accordance with an embodiment of the present invention.

Referring now to FIG. 17, there is shown another embodiment of the present invention, which constitutes a measuring device 131 that can be used to determine the thickness of the vessel wall 132. The measuring device 131 includes an anvil 133 at its distal end. The anvil base 134 at the proximal side of the anvil 133 is surrounded by an anvil edge 135, and the anvil 133 is attached to the instrument by support shaft 136. The anvil 133 is shown in FIG. 17 as having a rounded distal tip that therefore requires an initial incision to be made in the vessel wall 132 with a separate scalpel and/or scissors in order to insert the anvil 133 into the vessel. However, the anvil 133 can take any shape, including having a sharp tip that facilitates one-step penetration into the vessel without the need for an initial incision to be made by a separate instrument.

The measuring device 131 includes a thumb button 137 that can be pushed into a central opening 138 in an outer cylindrical member 139 that surrounds the inner cylindrical member 143. The inner cylindrical member 143 surrounds the support shaft 136 for the anvil 133, and can be slid proximally and distally along the support shaft 136. A hollow cylindrical plunger 140 is attached proximally to the thumb button 137 and extends into the central opening 138 of the outer cylindrical member 139. A pin 141 extends through slot 142 formed in the hollow cylindrical portion 110 of the thumb button 106 and is secured to the finger grip body 108. The slot 142 slides across the pin 141 as the thumb button 137 is pushed into the central opening 138 of the outer cylindrical member 139. The pin 141 restricts rotation and the extent to which the thumb button 137 can be pushed into the central opening 138 in the outer cylindrical member 139. The support shaft 136 does not move as the thumb button 137 is pushed into the outer cylindrical member 139 because the support shaft 136 is secured to the outer cylindrical member 139 by the pin 141. However, the inner cylindrical member 143 slides along the support shaft 136 as the thumb button 137 is pushed.

In accordance with present invention, the plunger 140 includes numerous graduated markings 145 that extend from the thumb button 137 longitudinally along the length of the outer surface of the plunger 140. The graduated markings 145 are positioned in measured increments along the plunger 140. In the preferred embodiment, the graduated markings 145 are positioned in one-half millimeter increments along the plunger 140. However, the graduated markings 145 may be organized in any other measurement increments, including fractional markings within every one-half millimeter increment. The graduated markings 145 facilitate measurement of the thickness of the vessel wall 132 located between the anvil and the distal end 144 of the inner cylindrical member 143.

Figure 19:
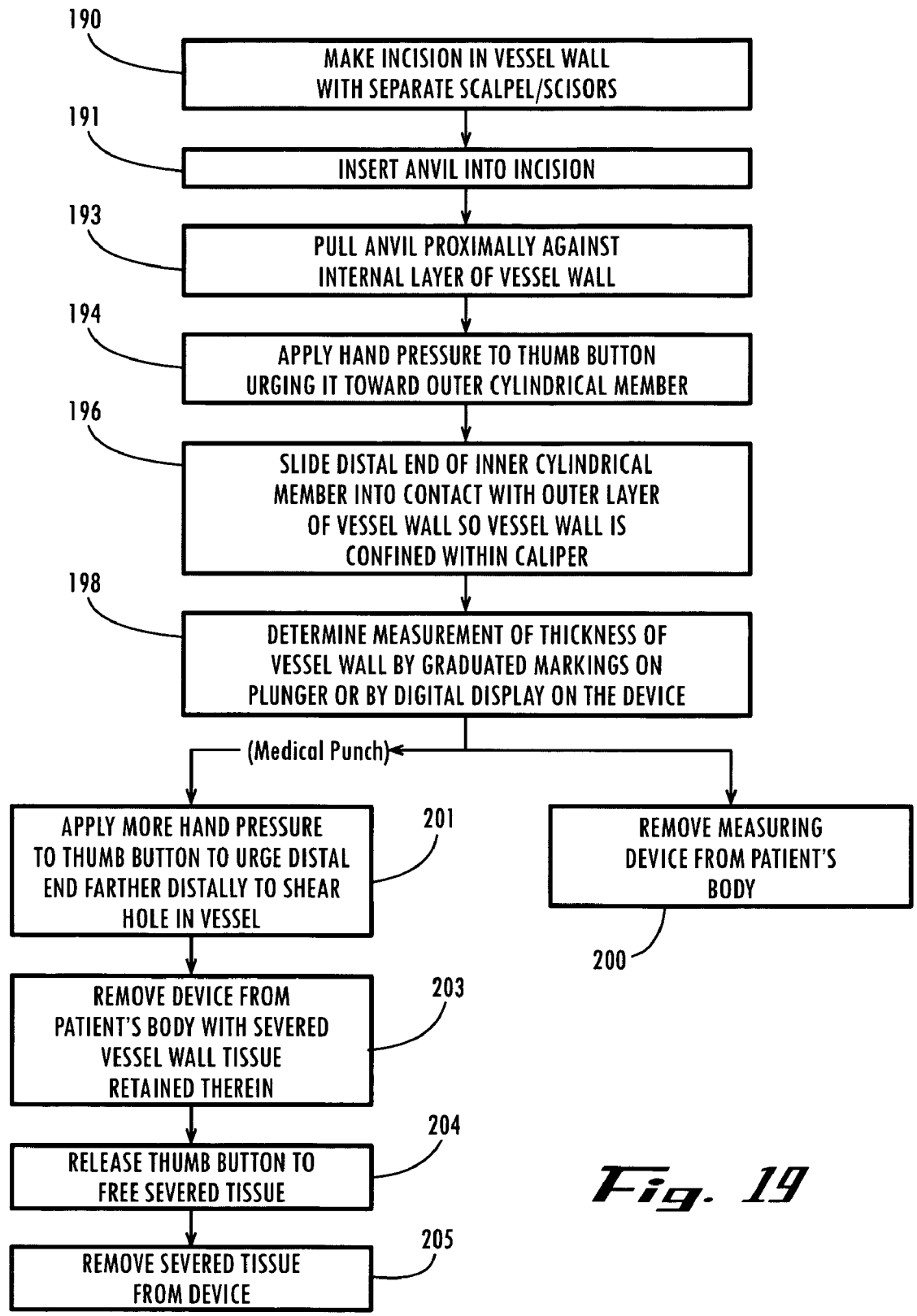
FIG. 19 is a flow chart illustrating the surgical procedure according to another method embodiment of the present invention.

There is shown a method embodiment of the present invention in the flow chart of FIG. 19 that will be described with reference to FIG. 17. In operation, an initial incision is made 190 in the vessel wall by a separate scalpel and/or scissors, and the anvil 133 of the measuring device 131 is inserted 191 into the incision. Once inserted, the surgeon moves the measuring device 131 proximally to pull the anvil 133 proximally 193 against the internal layer of the vessel wall 132. Then, in response to hand pressure applied 194 to the thumb button 137 toward the central opening 138 of the outer cylindrical member 139, the distal end 144 of the inner cylindrical member 143 slides axially 196 toward the vessel wall 132. The thumb button 137 is depressed until the surgeon feels the resistance of the external layer of the vessel wall 132 against the distal end 144 of the inner cylindrical member 143, thereby confining the vessel wall 132 between the anvil base 134 and the distal end 144. The anvil base 134 and the distal end 144 of the inner cylindrical member 143 together form a caliper 146 for measuring the thickness of the vessel wall 132. The measurement can then be determined 198, and the device removed 198 from the patient's body.

The distance between the anvil base 134 and the distal end 144 of the inner cylindrical member 143 represents the thickness of the vessel wall 132. Accordingly, the distance that the plunger 140 advances into the central opening 138 of the outer cylindrical member 139 when the thumb button 137 is depressed to advance the distal end 144 also represents the thickness of the vessel wall. Thus, the distance that the plunger 140 and the graduated markings 145 advance into the outer cylindrical member 139 establishes the measurement value shown on the graduated marking 145 visible just above the point where the plunger 140 enters the outer cylindrical member 139. This measurement value approximately equals to the thickness of the vessel wall.

In another embodiment of the measuring device 131, the measurement of the thickness of the vessel wall 132 is determined 198 through the use of electronics, and the measurement value is indicated on a digital display 147. The digital display 147 can be an alternative or a supplement to the graduated markings 145 for enhanced accuracy of measurement. A digital display 147 is shown in FIG. 17 located on the outer surface of the outer cylindrical member 139, but the digital display 147 can be located on any convenient and visible surface on the device. In the same manner as described in the previous embodiment, the anvil 133 is inserted into an incision in the vessel wall 132 and pulled proximally against the internal tissue layer. The thumb button 137 is depressed to advance the distal end 144 of the inner cylindrical member 143 to a point where it is in contact with the vessel wall 132. The thickness measurement is determined, for example by a linear digital encoder that senses linear displacement to produce a corresponding number of output pulses that are counted and displayed with an appropriate scaling factor to indicate thickness directly.

In another embodiment of measuring device 131, the device also constitutes a medical punch. An incision is made 190 and the anvil 133 is inserted 191 into the vessel wall 132 in the same manner as previously described herein. However, the distal end 144 of the inner cylindrical member 143 includes a cutting edge 148. The measurement of the thickness of the vessel wall 132 located within the caliper 146 is determined 198 by reading the graduated markings 145 and/or the digital display 147. The surgeon can then put more pressure 201 on the thumb button 137 to further advance the cutting edge 148. The cutting edge 148 cooperates with the anvil edge 135 and is advanced over the anvil edge 135 to achieve a clean and accurate cut of vessel tissue. Additionally, the plug of tissue thus severed remains anchored on the anvil base 134 for convenient retrieval from within the vessel upon withdrawal 203 from the vessel of the entire assembly of anvil 133 and inner cylindrical member 143. The thumb button 137 can be released 204 and the severed tissue removed 205 from the punch.

Therefore, the medical punch of the present invention allows for one- or two-step punching to form a clean and accurate aperture in a vessel wall, while minimizing tearing of the tissue and awkward manipulation of the punch during insertion of a wide anvil structure into the vessel. The measuring device of the present invention provides a simple and accurate method for determining vessel wall thickness. Additionally, the same measuring device can be used to form a clean aperture in the vessel without the need for and risks of introducing additional devices into the patient.

What is claimed is:

1. A medical punch comprising:
   a first member with a distal end and a proximal end having attached to the distal end thereof a penetrating structure including an anvil base surrounded by an anvil edge; the penetrating structure including at least two longitudinally divided sections that are disposed in close proximity for relative longitudinal movement, wherein at least two of said at least two longitudinally divided sections each include a portion of said anvil edge; and
   a second member having a distal end thereof disposed to cooperate with the anvil edge of the penetrating structure to provide therewith a shearing action in response to relative translational movement between the distal end of the second member and the anvil edge of the penetrating structure.

2. The medical punch according to claim 1 in which at least one of the sections of the penetrating member is disposed for independent relative translational movement proximally and distally.

3. The medical punch according to claim 1 in which the penetrating member is attached to a support shaft that is divided longitudinally into at least two sections that are disposed in close proximity for relative translational movement.

4. The medical punch of claim 3 in which the at least two sections of the support shaft correspond with the at least two sections of the penetrating member and the sections of the support shaft are disposed for relative translational movement proximally and distally.

5. The medical punch according to claim 1 including a distal tip of the penetrating structure and including a transition segment with a substantially conical surface that diverges in a direction going from the distal tip toward the anvil edge.

6. The medical punch according to claim 5 including a cylindrical segment that extends proximally from the distal tip of the penetrating structure toward the substantially conical surface of the transition segment.

7. The medical punch according to claim 6 in which at least one section of the penetrating structure is disposed for translation distally or proximally relative to one or more other section including to a position in which the cylindrical segment of at least one section is in proximity to the anvil edge portion of at least one other section.

8. The medical punch according to claim 5 in which the penetrating structure includes at least one cutting device extending longitudinally and distally from the distal tip of one of the sections to the anvil base.

9. The medical punch according to claim 8 in which the cutting device is a sharp blade.

10. The medical punch according to claim 9 in which the blade is substantially flat and extends along the penetrating structure between the at least two sections.

11. The medical punch according to claim 5 in which the distal tip on the penetrating structure has a substantially rounded surface.

12. The medical punch according to claim 5 in which the distal tip on the penetrating structure extends distally to a sharp point.

13. The medical punch according to claim 1 in which at least one section of the penetrating structure is disposed for translation distally or proximally relative to one or more other sections including to a position in which the distal tip of at least one section is in proximity to the anvil edge of at least one other section.

14. The medical punch according to claim 1 in which at least one section of the penetrating structure is disposed for translation distally or proximally relative to one or more other section including to a position in which the anvil edge portion of at least one section is in proximity to the anvil edge portion of at least one other section.

15. The medical punch according to claim 1 including a finger grip coupled to the first member and a thumb button coupled to the second member for establishing the relative translational movement in response to manual movement of the thumb button toward the finger grip.

16. The medical punch according to claim 15 including a resilient member disposed to exert resilient bias force in a direction urging longitudinal separation of the thumb button and the finger grip.

17. The medical punch according to claim 1 in which the anvil base of the penetrating structure facilitates engagement of tissue to be sheared between the anvil edge of the penetrating structure and the distal end of the second member.

18. The medical punch according to claim 1 in which the distal end of the second member includes a sharp edge.

19. A medical punch comprising:
   a first member with a distal end and a proximal end having attached to the distal end thereof a penetrating structure including an anvil base surrounded by an anvil edge; the penetrating structure including at least two longitudinally divided sections that are disposed in close proximity for relative longitudinal movement, a distal tip of the penetrating structure including a transition segment with a substantially conical surface that diverges in a direction going from the distal tip toward the anvil edge, and a cylindrical segment that extends proximally from the distal tip of the penetrating structure toward the substantially conical surface of the transition segment; and
   a second member having a distal end thereof disposed to cooperate with the anvil edge of the penetrating structure to provide therewith a shearing action in response to relative translational movement between the distal end of the second member and the anvil edge of the penetrating structure.

20. The medical punch according to claim 19 in which at least one section of the penetrating structure is disposed for translation distally or proximally relative to one or more other section including to a position in which the cylindrical segment of at least one section is in proximity to the anvil edge of at least one other section.

21. A medical punch comprising:
   a first member with a distal end and a proximal end having attached to the distal end thereof a penetrating structure including an anvil base surrounded by an anvil edge; the penetrating structure including at least two longitudinally divided sections that are disposed in close proximity for relative longitudinal movement, a distal tip of the penetrating structure including a transition segment with a substantially conical surface that diverges from the distal tip to the anvil edge, and in which the distal tip on the penetrating structure has a substantially rounded surface; and a second member having a distal end thereof disposed to cooperate with the anvil edge of the penetrating structure to provide therewith a shearing action in response to relative translational movement between the distal end of the second member and the anvil edge of the penetrating structure.

22. A medical punch comprising:

a first member with a distal end and a proximal end having attached to the distal end thereof a penetrating structure including an anvil base surrounded by an anvil edge; the penetrating structure including at least two longitudinally divided sections, each including a portion of the anvil edge, that are disposed in close proximity for relative longitudinal movement;

a second member having a distal end thereof disposed to cooperate with the anvil edge of the penetrating structure to provide therewith a shearing action in response to relative translational movement between the distal end of the second member and the anvil edge of the penetrating structure; and a finger grip coupled to the first member and a thumb button coupled to the second member for establishing the relative translational movement in response to manual movement of the thumb button toward the finger grip.

23. The medical punch according to claim 22 including a resilient member disposed to exert resilient bias force in a direction urging longitudinal separation of the thumb button and the finger grip.

* * * * *